US006414484B1

United States Patent
Kim et al.

(10) Patent No.: US 6,414,484 B1
(45) Date of Patent: *Jul. 2, 2002

(54) APPARATUS AND METHOD FOR SIMULTANEOUS DETECTION OF EMBEDDED REINFORCEMENT IN CONCRETE

(75) Inventors: Young Joo Kim; Hahn Gue Moon, both of Daejeon (KR)

(73) Assignee: Korea research Institute of Standards and Science, Daejeon (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,479

(22) Filed: Apr. 28, 1999

(30) Foreign Application Priority Data

Jun. 25, 1998 (KR) .............................................. 98-24197

(51) Int. Cl.[7] .......................... G01N 27/72; G01R 33/12
(52) U.S. Cl. ...................................................... 324/243
(58) Field of Search .......................... 324/243, 67, 228, 324/229, 233, 239–242, 326, 260

(56) References Cited

U.S. PATENT DOCUMENTS

| 3,882,374 | A | * | 5/1975 | McDaniel | 324/243 |
|---|---|---|---|---|---|
| 4,686,471 | A | * | 8/1987 | Morita et al. | 324/243 |
| 4,894,617 | A | * | 1/1990 | Urbani | 324/243 |
| 4,931,730 | A | * | 6/1990 | Olsen et al. | 324/243 |
| 5,021,738 | A | * | 6/1991 | Vernon et al. | 324/242 |
| 5,992,241 | A | * | 11/1999 | Posgay et al. | 324/209 |

* cited by examiner

Primary Examiner—Jay Patidar
(74) Attorney, Agent, or Firm—Finnegan, Henderson, Farabow, Garrett & Dunner, L.L.L.P (57) ABSTRACT

The present invention relates to a multicoil probe for simultaneous detection of size and depth of embedded reinforcement in concrete and method of detection using the same and more particularly, to a multicoil probe having sensing coils which are mounted in the inside and outside of an exciting coil and a method of detecting size and depth of embedded reinforcement in concrete using the same.

4 Claims, 7 Drawing Sheets

APPARATUS AND METHOD FOR SIMULTANEOUS DETECTION OF EMBEDDED REINFORCEMENT IN CONCRETE

BACKGROUND OF THE INVENTION

1. Field of the Invention

The present invention relates to a multicoil probe for simultaneous detection of size and depth of embedded reinforcement in concrete and method of detection using the same and more particularly, to the multicoil probe having sensing coils which are mounted in the inside and outside of an exciting coil and the method for detecting size and depth of embedded reinforcement in concrete using the same.

2. Description of the Prior Art

Generally, the reinforcements adequate to the designed structural strength are embedded in the reinforced concrete construction such as building.

When the structural safety test on the reinforced concrete construction is performed, the reinforcement embedded in the reinforced concrete construction should be detected using a reinforcement detector designed to detect its depth.

A typical reinforcement detector consists of a probe and an analysis device; the former is fabricated by a coil for reaction with the reinforcement in the concrete, and the latter with a control lever may serve not only as a power source, but also as input of size of reinforcement and detection of signal from the probe.

Figure 3A:
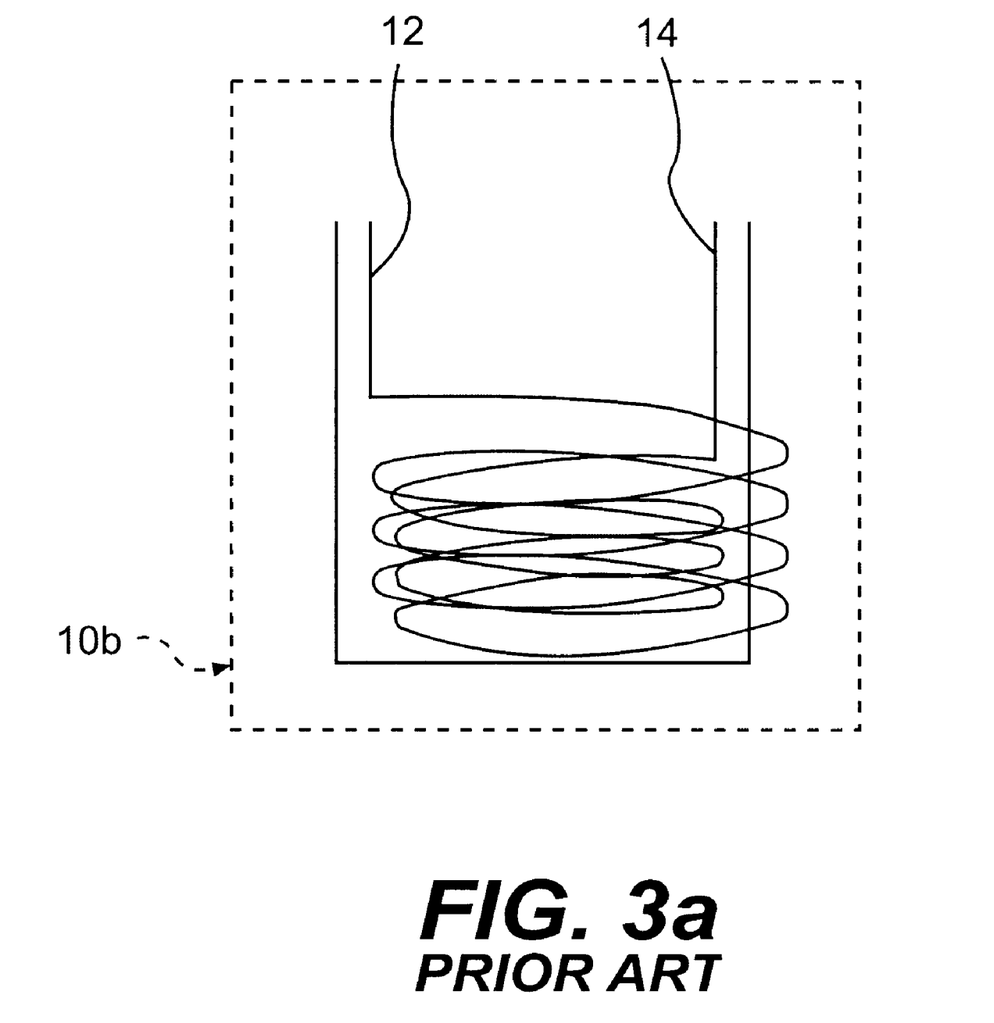
Figure 3B:
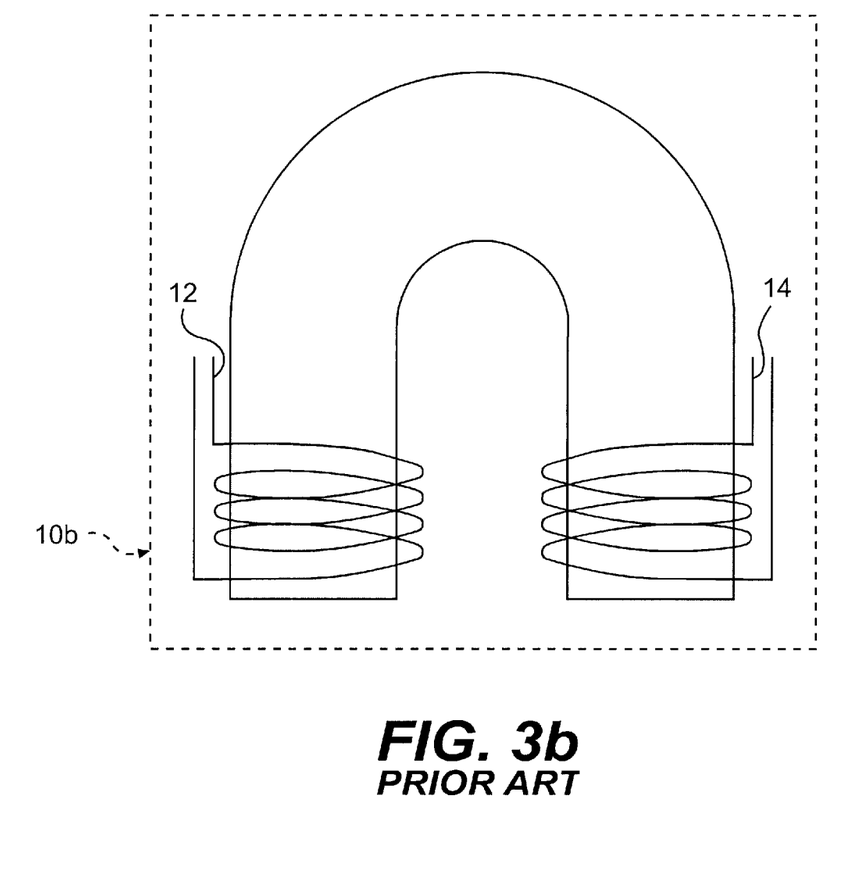

Referring to FIGS. 3a and 3b, the conventional probe of reinforcement detector is briefly described as follows:

With one exciting coil 12 in a housing in a certain size, the probe 10b has one sensing coil 14 mounted in the inside or outside of exciting coil 12.

Therefore, a control lever on the reinforcement detector is adjusted by the sizes of reinforcements embedded in concrete.

Commonly, one is aware of the size of the reinforcements embedded in concrete by referring to some design of the reinforced concrete building; or, the size of the reinforcements may be adjusted by assumption.

As the probe 10b is tightly held to the reinforced concrete for detection, the exciting coil 12 within the probe 10b is reacted with the reinforcement embedded in the concrete, thereby forming a magnetic field in the inside and outside of exciting coil 12.

After the sensing coil 14 detects the magnetic field formed from the inside and outside of exciting coil 12 as an induced voltage, such voltage is delivered to the analysis device.

The induced voltage released from the sensing coil 14 is detected and a analyzed by the analysis device and thus, the analysis device shows the depth of the reinforcement in values on its display.

However, the conventional probe 10b has some disadvantages as follows:

The reactivity of the probe 10b varies differently depending upon the depth and size of embedded reinforcement; namely, the thicker its size is and the shallower the embedded depth is, the larger the reactability of the probe 10b becomes.

In case where a thick reinforcement is deeply embedded in the reinforced concrete construction and a thin reinforcement is shallowly embedded in the reinforced concrete, the probe will have a similar reactability.

In this context, a majority, of the conventional probe 10b may indicate a value related to the embedded depth or size of the reinforcement, when either depth or size of the reinforcement may be given.

If one is unaware of the embedded depth and size of the reinforcement, he/her has no choice but to presume them through repeated detections over a long period of time and if this is the case, the detection values will have little accuracy.

SUMMARY OF THE INVENTION

To overcome the above shortcomings, an object of the present invention is to provide a multicoil probe for simultaneous detection of size and depth of embedded reinforcement in concrete, wherein it comprise: in a multicoil probe where the plural number of sensing coils are mounted in the inside and outside of exciting coil, the multicoil probe may serve to detect the different distribution of magnetic field formed in the inside and outside of the exciting coil, as the induced voltage value, in consideration of the fact that the distribution of magnetic field formed in the inside and outside of the exciting coil varies differently depending on the size and depth of the reinforcements embedded in the concrete.

Another object of the present invention is to provide a method for simultaneous detection of size and depth of embedded reinforcement in concrete, by comparing the actually-measured induced voltage values using the multicoil probe with the plural number of sensing coils, with those in a pre-prepared table showing each depth and size of the embedded reinforcements, even though one is unaware of the size and depth of the unknown reinforcement.

Figure 1:
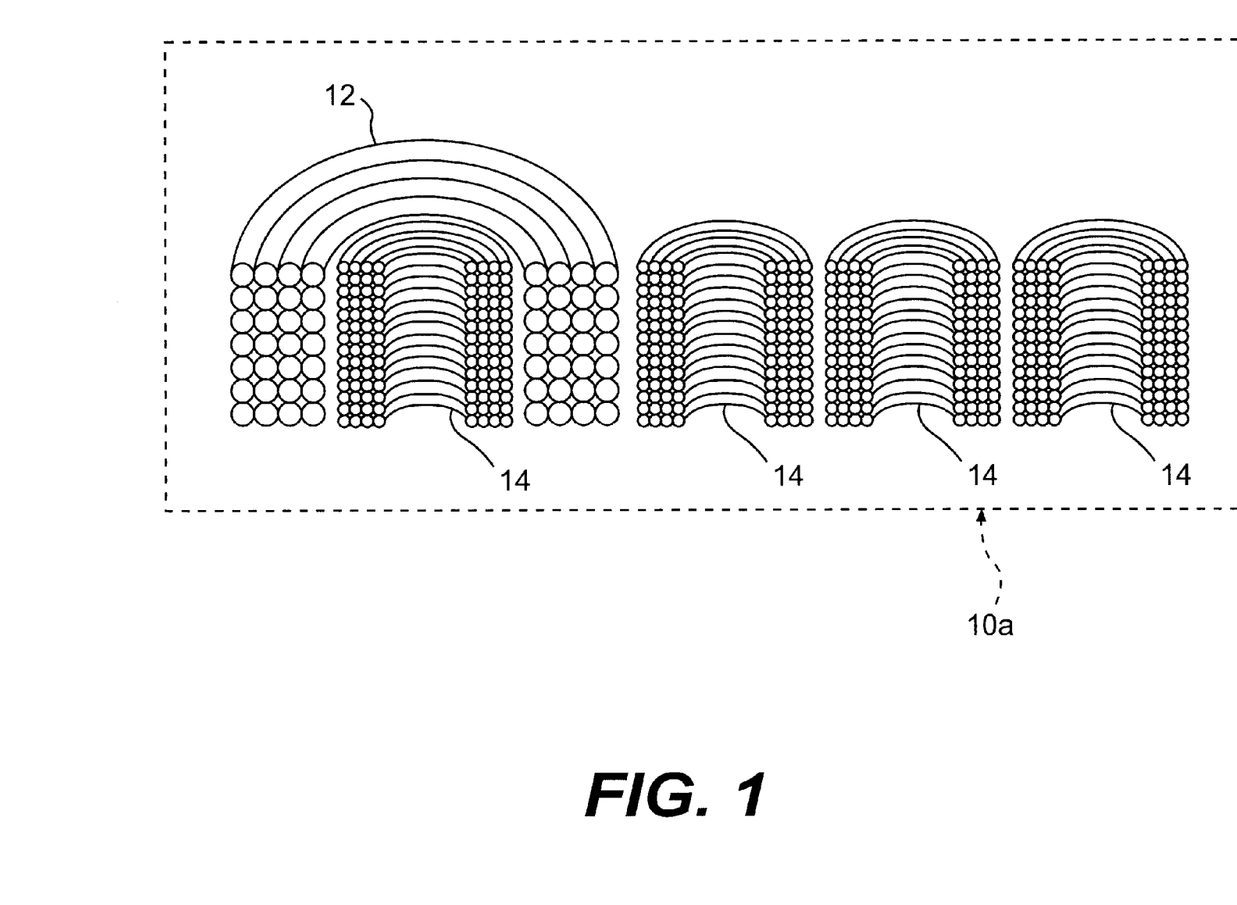
FIG. 1 is a schematic view showing a multicoil probe which can simultaneously detect the size and depth of reinforcement in concrete.
Figure 2A:
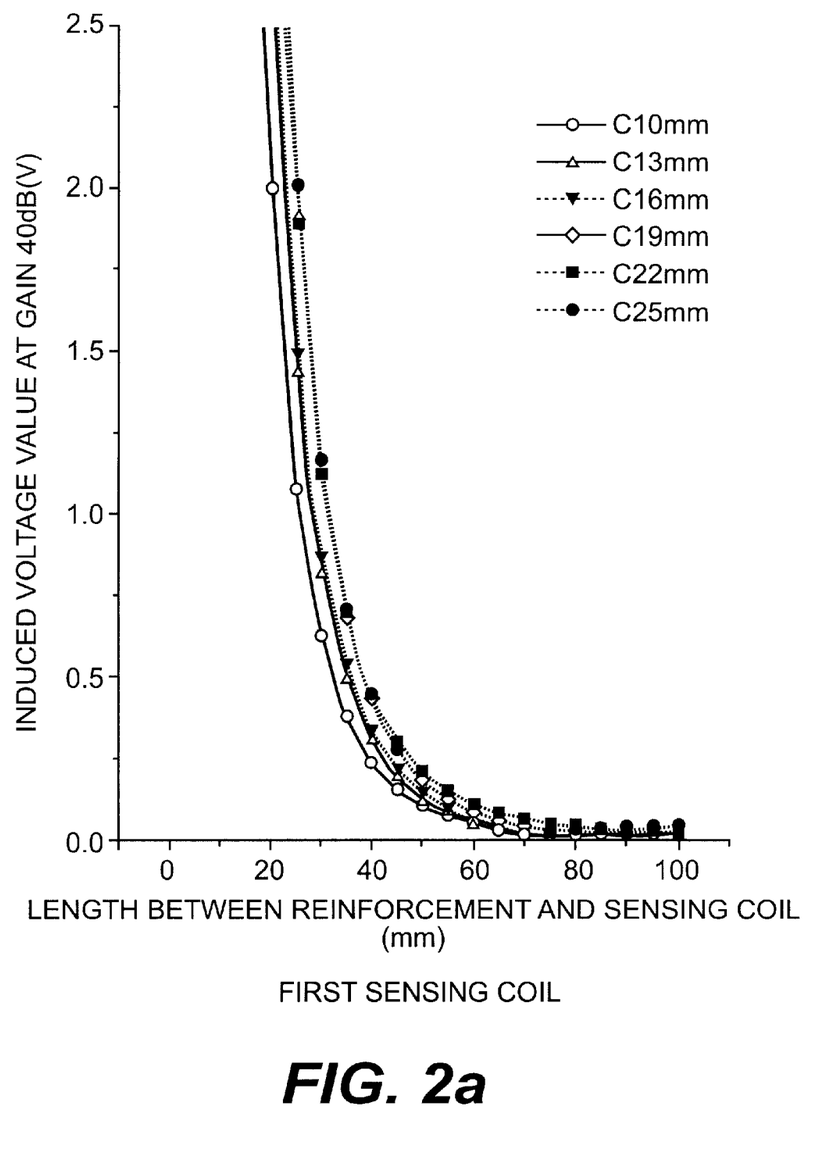
FIGS. 2a, 2b, 2c, and 2d are some graphs showing the induced voltage values depending upon the depth of reinforcements detected by sensing coils in the inside and outside of multicoil probe, which can simultaneously detect the size and depth of reinforcement in concrete according to the present invention.
Figure 2B:
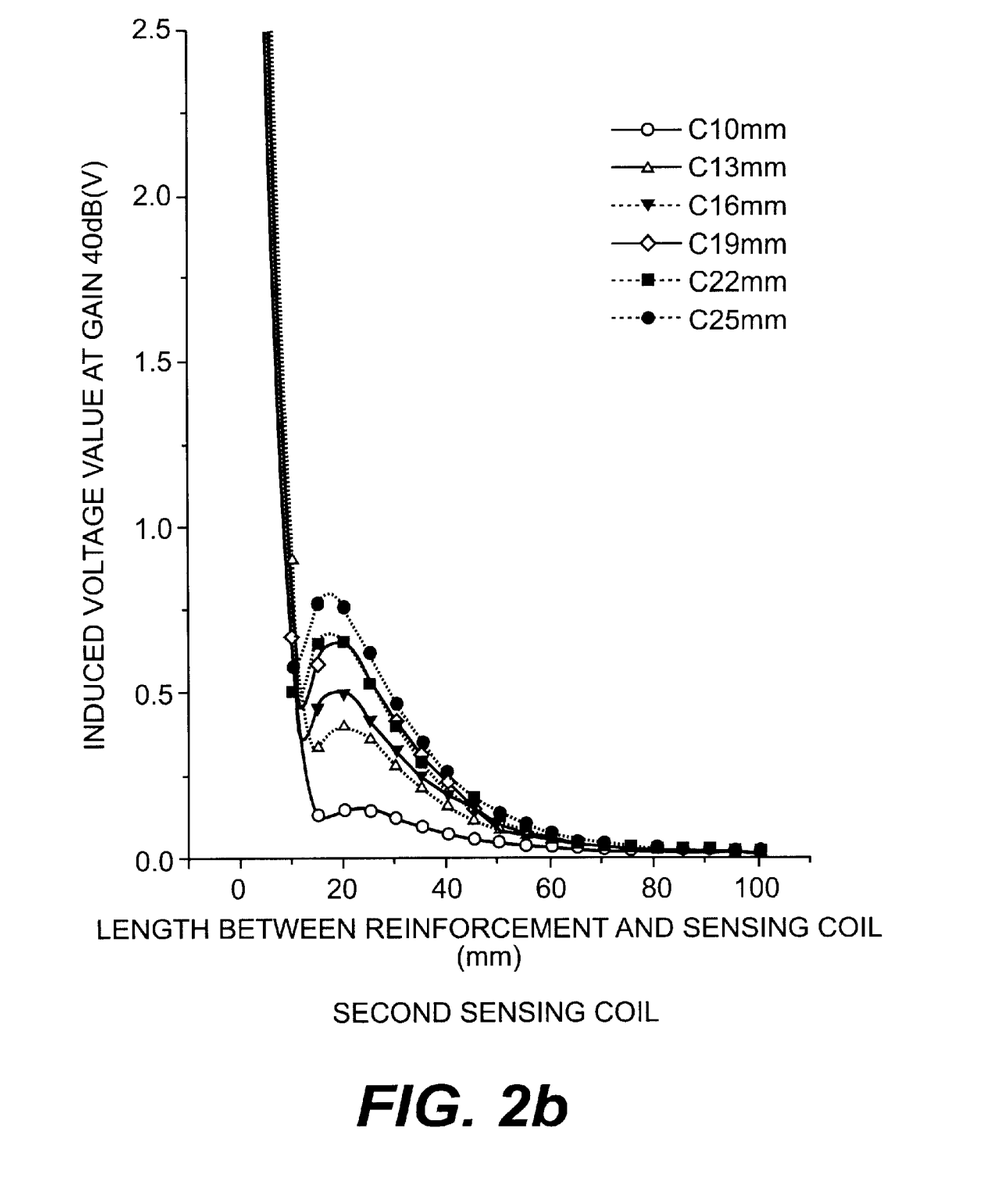
Figure 2C:
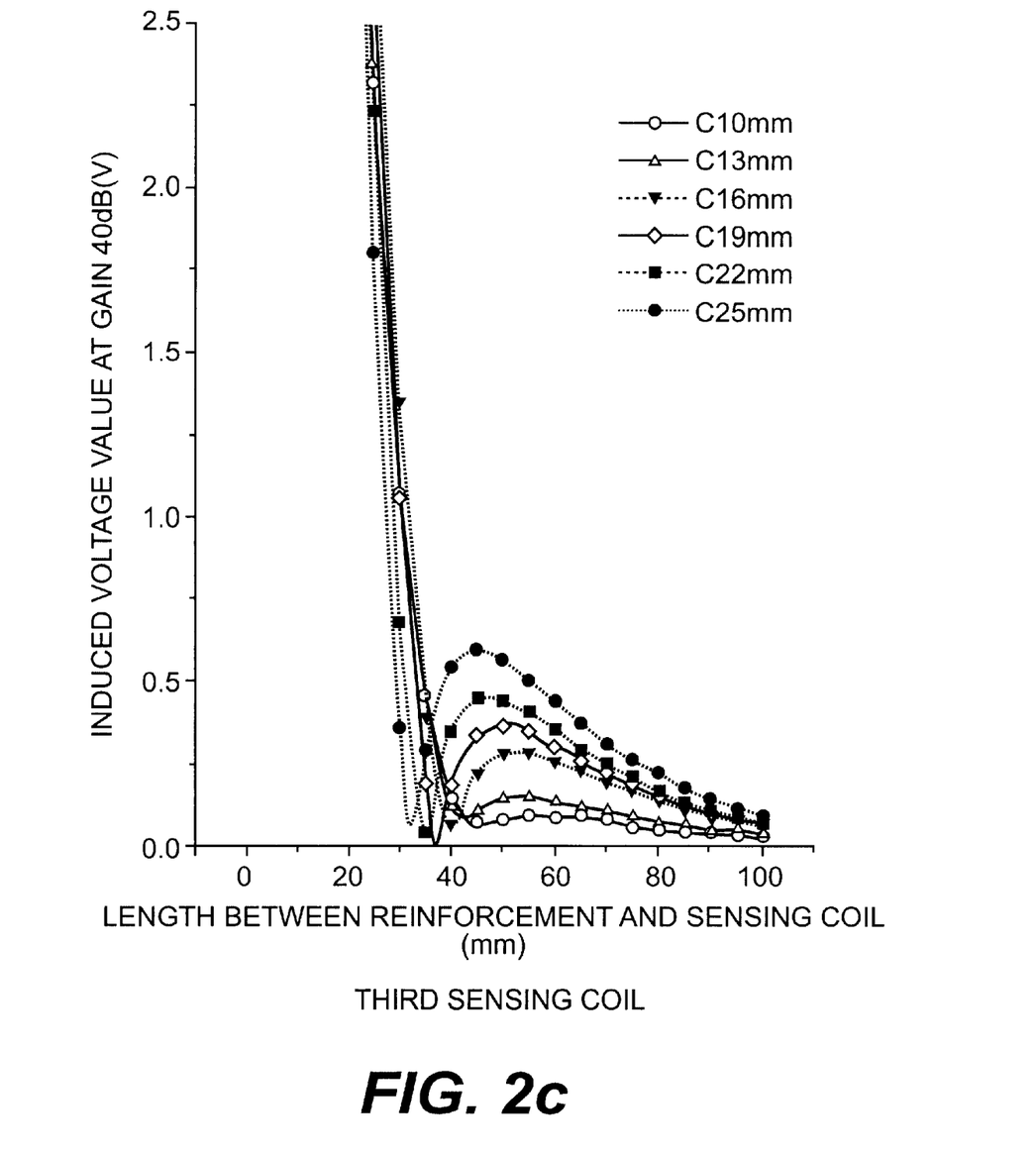
Figure 2D:
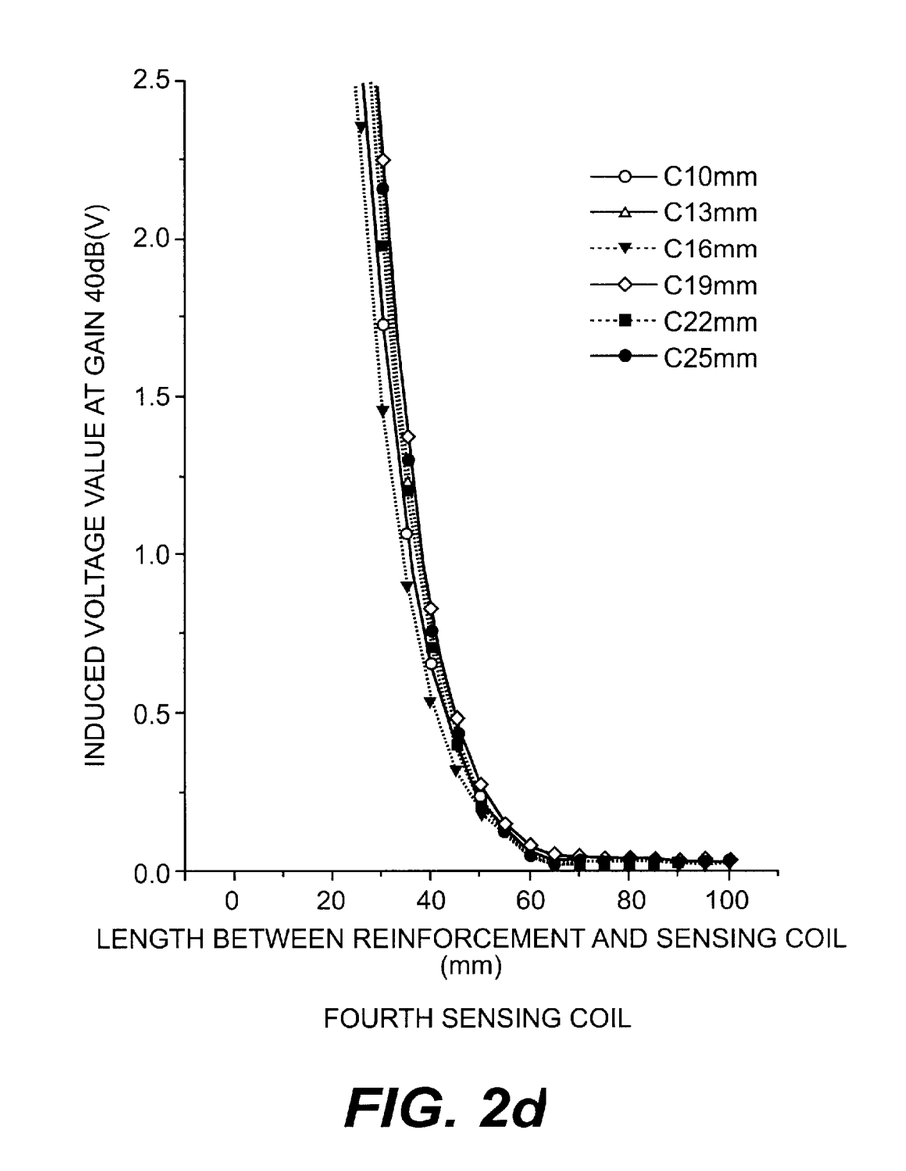

To achieve the above object, a multicoil probe of the present invention is constructed in such a manner that the plural number of the sensing coil 14 are mounted in the inside and outside of exciting coil in the probe 10a so as to measured the induced voltage values.

According to the present invention, the method for simultaneous detection of size and depth of embedded reinforcement is characterized by the following subsequent steps of:

a) pre-preparing a table for the induced voltage values which may vary differently depending upon the depth and size of embedded reinforcements, and measuring the induced voltage values on the unknown reinforcements in the concrete using the sensing coil 14 positioned in the inside and outside of exciting coil 12 of the multicoil probe 10a;

b) comparing the induced voltage values of the unknown embedded reinforcement, so detected, with those in the prepared table showing each depth and size of the embedded reinforcements, and;

c) determining the size and depth of the unknown reinforcement whose induced voltage values, so detected, are in the range established in the prepared table.

BRIEF DESCRIPTION OF THE DRAWINGS

The accompanying drawings, which are incorporated in and constitute a part of the specification, illustrate an embodiment of the invention, and together with the description, serve to explain the principles of the invention.

FIG, 3a, 3b are a schematic view showing the conventional probe for detection of reinforcement in concrete.

DETAILED DESCRIPTION OF THE PREFERRED EMBODIMENT

Reference is made in detail to the preferred embodiment of the present invention, an example of which is illustrated in the accompanying drawings.

According to this invention, a multicoil probe for simultaneous detection of size and depth of embedded reinforcement in concrete comprises the plural number of a sensing coil 14 in the inside and outside of the exciting coil mounted in the probe 10a.

It is preferred that one sensing coil 14 is mounted in the inside of exciting coil 12, while at least one sensing coils are mounted in the outside of exciting coil 12.

According to this invention, a method for simultaneous detection of size and depth of embedded reinforcement is characterized by the following subsequent steps of:

a) pre-preparing a table for the induced voltage values which may vary differently depending upon the depth and size of embedded reinforcements in concrete;

b) measuring the induced voltage values on the unknown reinforcements in the concrete using the sensing coil 14 mounted in the inside and outside of exciting coil 12 of the multicoil probe 10a;

c) comparing the induced voltage values of the unknown embedded reinforcement, so measured, with those in the pre-prepared table showing each depth and size of the embedded reinforcements; and d) determining the size and depth of the unknown reinforcement whose induced voltage values, so measured, are in the range established in the prepared table.

In an effort to obtain a more accurate and clear value, the step of measuring the induced voltage values on the unknown reinforcement is performed in such a manner that when the induced voltage values measured from the first coil of the sensing coils 14 are in the several ranges established by the pre-prepared table, measurement of the induced voltage value with other sensing coils is subsequently carried out until the value is in the one range established pre-prepared table.

Referring to the drawing, FIG. 1 is an schematic view showing a multicoil probe according to the present invention.

Housing (non-illustrated) in limitless shapes is formed in the outside of multicoil probe 10a, and the exciting coil 12 is mounted in the inside of the housing 10a; as shown in FIG. 1, one sensing coil 14 is mounted in the inside of exciting coil 12, and sensing coils 14 are mounted in its outer part.

More specifically, one sensing coil 14 is mounted in the inside of exciting coil 12, while one or more sensing coil 14 is mounted in the outside of exciting coil 12; namely, in case of the sensing coil 14, at least two or more coils are necessary and these coils may be mounted by four.

The reason why the sensing coils are mounted in the inside and outside of exciting coil 12 is described as follows:

Generally, the inside and outside distribution of a magnetic field generated around the exciting coil 12 installed in all reinforcement probes are entirely different, in that when the sensing coil 14 attached to the inside and outside of exciting coils approaches the reinforcement, respectively, the induced voltage values becomes different.

A method for simultaneously measuring the size and depth of reinforcement embedded in concrete using the aforementioned multiprobe is described as follows:

First, the depth on the reinforcements of all sizes is detected in advance and then, a chart involving the induced voltage values depending upon the size and depth of the reinforcements are prepared.

The data is prepared in the following manner through the previous detection of depths on all sizes of reinforcement and induced voltage values.

Once a pilot concrete structure is first manufactured in such a manner that standardized reinforcements in various forms are embedded in concrete per different types of depth, one can be aware of the depth of reinforcement in each size. Then, the multicoil probe 10a for detection of the induced voltages is closely attached to a side of pilot concrete structure for the detection of induced voltage values related to the size and depth of reinforcements.

Therefore, the pre-prepared test data (size and depth of the reinforcement, changes in the induced voltages) prove to be very accurate and reliable, in that the values, so detected, are obtained from the pilot concrete structure where reinforcements in various forms are embedded in concrete per different types of depth.

The method for measuring the induced voltages of unknown reinforcements in the concrete using the multicoil probe 10a will be explained in more detail from some examples afterwards.

The actual test data (size and depth of the reinforcement, changes in the induced voltages) are stored at the analysis device of the detector for the comparison with the pre-prepared test data.

By way of some examples, the size and depth of reinforcements and their induced voltage values are shown in the following table 1.

TABLE 1

| No. | Size of reinforcement (mm) | Embedded depth of reinforcement (mm) | First sensing coil | Second sensing coil | Third sensing coil | Fourth sensing coil |
| --- | --- | --- | --- | --- | --- | --- |
| 1 | 10 | 51–52 | 1028–955 | 604–585 | 96–90 | 237–228 |
| 2 | 13 | 55–56 | 1036–960 | 575–545 | 163–158 | 159–150 |
| 3 | 16 | 56–57 | 1041–966 | 634–591 | 61–63 | 98–77 |
| 4 | 19 | 59–60 | 1075–1010 | 710–679 | 293–287 | 90–86 |
| 5 | 22 | 59–60 | 1087–1017 | 708–678 | 283–266 | 44–37 |
| 6 | 25 | 61–62 | 1075–1009 | 746–705 | 355–318 | 42–38 |

Then, the multicoil probe 10a is connected, via a wire for signal transmission, to the analysis device having the above table 1. The multicoil probe 10a for detection of the induced voltages is closely attached to a side of pilot concrete structure for the detection of induced voltage values related to the size and depth of unknown reinforcements. The magnetic fields in the inside and outside of the exciting coil 12 are formed differently, when the multicoil probe 10a is attached to the unknown reinforcement in the concrete.

Further, due to the different distribution of magnetic field generated in the inside and outside of the exciting coil 12, the plural number of sensing coils (four sensing coils are provided for description of Example) located in the inside and outside of exciting coil 12 detects the magnetic fields simultaneously as changes in the induced voltage, which are transmitted to the analysis device via a wire for signal transmission.

Hence, the changes in the induced voltage values detected by the four sensing coils, are shown as illustrated in FIG. 2a through FIG. 2d.

We can suppose the results of the induced voltage on the reinforcements detected by the four sensing coils, as those shown in the following table 2.

TABLE 2

| First sensing coil | Second sensing coil | Third sensing coil | Fourth sensing coil |
|---|---|---|---|
| 1027 | 574 | 162 | 158 |

The induced voltages on the unknown reinforcements obtained from the table 2 are compared with those in the table 1.

Hence, the above comparison is actually carried out in an analysis device of the detector.

As noted in the table 2, the induced voltage of the first sensing coil to the unknown reinforcement is 1027, which is compared with that of the first sensing coil in the table 1.

Such comparison shows that the induced voltage value of 1027 in the first sensing coil to the unknown reinforcement belongs to the range of the induced voltage values of all the first sensing coils.

In this context, one becomes unaware of the accurate size and depth of the unknown reinforcement to be detected, since the induced voltage value of 1027 in the first sensing coil to the unknown reinforcement belongs to the range of the induced voltage values of all the first sensing coils.

If one becomes unaware of the size and depth of the unknown reinforcement in the first sensing coil, the induced voltage value of the second sensing coil (table 2) is compared with that of the second sensing coil (table 1).

The induced voltage value of 574 in the second sensing coil to the unknown reinforcement (table 2) is compared with that of the second sensing coil (table 1).

In this manner, the induced voltage value of 574 in the second sensing coil (table 2) is in the range of 575~545 in the second sensing coil of No. 2 reinforcement (table 1), being far from the induced voltage values of the second sensing coils of Nos. 1, 3 and 6.

Therefore, one is aware that the unknown reinforcement is the same one as of No. 2 reinforcement (size: 13 mm, depth: 55–56 mm), which is in the range of 575–545 as the induced voltage value of the second sensing coil, whereby the size and depth of the unknown reinforcement is finally determined as 13 mn and 55–56 mm, respectively.

In case that the plural number of reinforcements having common induced voltage values still exists, when the induced voltage value of the second sensing coil (table 2) is compared with that of the second sensing coils (table 1), the induced voltage values in the third and fourth sensing coils (table 2) are continuously compared with those of the third and fourth sensing coils (table 1) in the same procedure above, thereby one can easily be aware of the size and depth of the unknown reinforcement.

As described in the above, a multicoil probe for simultaneous detection of size and depth of embedded reinforcement in concrete and method of detection using the same according to the present invention has an advantageous, since the size and depth of the unknown reinforcement may be easily and conveniently detected by the plural number of sensing coils which may serve to detect the different distribution of magnetic field generated in the inside and outside of the exciting coil, as the induced voltage value.

What is claimed is:

1. A multicoil detector for simultaneous detection of size and depth of an embedded reinforcement comprising:

an exciting coil having a lumen;

a first sensing coil located within the lumen of the exciting coil;

a second sensing coil eccentrically spaced from the exciting coil; and an analysis device to measure induced voltages in the first and second sensing coils and to determine a size and depth of the embedded reinforcement based on a table of values arranged into a plurality of established ranges according to size and depth.

2. The multicoil detector according to claim 1, wherein at least one additional sensing coil is eccentrically spaced from the exciting coil.

3. A method for simultaneous detection of size and depth of an embedded reinforcement comprising the steps of:

preparing a table of induced voltage values arranged into a plurality of established ranges according to size and depth;

measuring induced voltage values on the embedded reinforcement using at least one sensing coil located inside of an exciting coil and at least one sensing coil mounted outside of the exciting coil;

comparing the measured induced voltage values with the established ranges in the prepared table;

determining a size and a depth of the embedded reinforcement based upon the measured induced voltage values being in at least one of the established ranges in the prepared table.

4. The method according to claim 3, wherein if the measured induced voltage values are in a plurality of the established ranges, then measuring induced voltage values continues until the measured induced voltage values are in one of established ranges in the prepared table.

* * * * *